(12) United States Patent
Bretz (10) Patent No.: US 11,351,583 B2
(45) Date of Patent: Jun. 7, 2022

(54) METHOD FOR BIOREMEDIATION OF HEAVY METAL CONTAMINATED SOIL

(71) Applicant: Walter A. Bretz, Nevada City, CA (US)

(72) Inventor: Walter A. Bretz, Nevada City, CA (US)

(*) Notice: Subject to any disclaimer, the term of this patent is extended or adjusted under 35 U.S.C. 154(b) by 406 days.

(21) Appl. No.: 16/191,877

(22) Filed: Nov. 15, 2018

(65) Prior Publication Data

US 2020/0156126 A1 May 21, 2020

(51) Int. Cl.
*B09C 1/10* (2006.01)
*G01N 33/24* (2006.01)

(52) U.S. Cl.
CPC .......... *B09C 1/105* (2013.01); *B09C 1/10* (2013.01); *G01N 33/24* (2013.01); *G01N 2033/243* (2013.01)

(58) Field of Classification Search
CPC .......... B09C 1/105; B09C 1/10; G01N 33/24; G01N 2033/243
See application file for complete search history.

(56) References Cited

U.S. PATENT DOCUMENTS

| | | | |
|---|---|---|---|
| 5,660,730 A | 8/1997 | Lucchese et al. | |
| 5,766,929 A * | 6/1998 | Orolin | B09C 1/10 210/611 |
| 6,107,079 A * | 8/2000 | Yadav | C12N 1/145 435/262.5 |
| 2010/0209988 A1* | 8/2010 | Hutchings | C12P 1/04 435/177 |
| 2018/0361444 A1* | 12/2018 | Franssen | B09C 1/10 |

FOREIGN PATENT DOCUMENTS

| | | |
|---|---|---|
| JP | 2005177740 A | 7/2005 |
| WO | WO-8607346 A1 * | 12/1986 ............. C02F 1/286 |

OTHER PUBLICATIONS

Turner, A., "Urban agriculture and soil contamination: an introduction to Urban Gardening" Pub 2009, Environmental Finance Center University of Louisville (Year: 2009).*
Gupta, et al "Current status of cow dung as a bioresource for sustainable development" Bioresour. Bioprocess, 3:28 p. 1-11 (Year: 2016).*
English translation of WO8607346 accessed Jan. 2021 (Year: 2021).*
Zhang, et al. "Organic wastes as carbon sources to promote sulfate reducing bacterialactivity for biological remediation of acid mine drainage" Minerals Engineering, 69 (2014) 81-90 (Year: 2014).*
Lu, "Heavy Metal Residues in Soil and Accumulation in Maize at Long-Term Wastewater Irrigation Area in Tongliao, China" Journal of Chemistry vol. 2015 p. 1-9 (Year: 2015).*
International Search Report and Written Opinion dated Apr. 17, 2020 for PCT/US2019/060398 filed Nov. 8, 2019; pp. 12.

* cited by examiner

*Primary Examiner* — William H. Beisner
*Assistant Examiner* — Danielle B Henkel
(74) *Attorney, Agent, or Firm* — Hoffman Warnick LLC (57) ABSTRACT

A method of treating a heavy metal contaminated soil including contacting the contaminated soil with a bioremediation mixture for a predetermined time such that the contaminated soil is anaerobically digested, wherein the contaminated soil contains one or more heavy metals, and wherein the anaerobically digested soil contains a lesser amount of the one or more heavy metals than the contaminated soil.

20 Claims, 6 Drawing Sheets

Specification includes a Sequence Listing.

METHOD FOR BIOREMEDIATION OF HEAVY METAL CONTAMINATED SOIL

TECHNICAL FIELD

The subject matter disclosed herein relates to bioremediation of contaminated soil. More specifically, various aspects described herein relate to methods for bioremediation of heavy metal contaminated soil.

SEQUENCE LISTING

The sequence listing contained in the electronic file entitled "WAB-0001-US_SequenceListing.txt" created Mar. 11, 2019, comprising 4 KB, is hereby incorporated herein by reference.

BACKGROUND

The continued industrialization of countries has led to extensive environmental contamination of soil and water. Among the pollutants, heavy metals pose a critical concern to human health and the global food chain. Heavy metals are natural constituents of the environment, but indiscriminate use for human purposes has altered their geochemical cycles and biochemical balance. This results in excess release of heavy metals such as cadmium, copper, lead, nickel, zinc etc. into the soil and aquatic environments. Prolonged exposure and higher accumulation of such heavy metals can have deleterious health effects on human and aquatic life. Thus, searching for innovative ways to remove metals from the environment has become a priority in the remediation field.

One promising strategy is phytoextraction, which is defined as the use of plants to take up pollutants from contaminated soil. The success of metal extraction depends on many factors, but key factors include a plant's ability to uptake and translocate metals to its stems and leaves, metal bioavailability and soil type. The efficiency of heavy metal phytoextraction may be supported by metal-resistant bacteria that belong to the plant growth-promoting bacteria (PGPB) group. PGPB include both rhizospheric (PGPR) and endophytic (PGPE) bacteria.

While anaerobic digesters are being developed for a variety of purposes today, current literature fails to identify the use of anaerobic digestion with specific bacteria/fungi consortiums to bioremediate soils contaminated with heavy metals. Advances in bioremediation technologies and additional strategies to explore the immense and valuable biological resources for bioremediation are needed.

BRIEF SUMMARY

Methods for bioremediation of heavy metal contaminated soil via anaerobic digestion are disclosed. In a first aspect of the disclosure, a method of treating a heavy metal contaminated soil includes: contacting the contaminated soil with a bioremediation mixture for a predetermined time such that the contaminated soil is anaerobically digested, wherein the contaminated soil contains one or more heavy metals, and wherein the anaerobically digested soil contains a lesser amount of the one or more heavy metals than the contaminated soil.

In a second aspect of the disclosure, a method of providing verified, decontaminated soil includes: anaerobically digesting a heavy metal contaminated soil by contacting the contaminated soil with a bioremediation mixture for a first predetermined time, planting at least one test crop in at least a portion of the anaerobically digested soil and allowing for crop maturation for a second predetermined time, testing at least a portion of the mature crop for a level of heavy metal contamination, and verifying that the anaerobically digested soil is decontaminated if the level of heavy metal contamination is zero or below a predetermined threshold.

BRIEF DESCRIPTION OF THE DRAWINGS

These and other features of this disclosure will be more readily understood from the following detailed description of the various aspects of the disclosure taken in conjunction with the accompanying drawings that depict various embodiments of the disclosure, in which.

It is noted that the drawings of the disclosure are not necessarily to scale. The drawings are intended to depict only typical aspects of the disclosure, and therefore should not be considered as limiting the scope of the disclosure. In the drawings, like numbering represents like elements between the drawings.

DETAILED DESCRIPTION

Detailed embodiments of the claimed methods are disclosed herein; however, it can be understood that the disclosed embodiments are merely illustrative of the claimed methods that may be embodied in various forms. The subject matter of this disclosure may, however, be embodied in many different forms and should not be construed as limited to the exemplary embodiments set forth herein. Rather, these exemplary embodiments are provided so that this disclosure will be thorough and complete and will fully convey the scope of this disclosure to those skilled in the art.

In the interest of not obscuring the presentation of embodiments of the present disclosure, in the following detailed description, some processing steps or operations that are known in the art may have been combined together for presentation and for illustration purposes and, in some instances, may have not been described in detail. In other instances, some processing steps or operations that are known in the art may not be described at all. It should be understood that the following description is rather focused on the distinctive features or elements of various embodiments of the present disclosure.

The subject matter disclosed herein relates to bioremediation of contaminated soil. More specifically, various aspects described herein relate to methods for bioremediation of heavy metal contaminated soil.

The present disclosure relates generally to bioremediation of contaminated soil, and more particularly, to methods for bioremediation of heavy metal contaminated soil via anaerobic digestion. As mentioned above, advances in bioremediation technologies are needed, including the use of anaerobic digestion with specific bacteria/fungi consortiums to bioremediate soils contaminated with heavy metals. Methods for bioremediation of heavy metal contaminated soil via anaerobic digestion are described below and with reference to the Tables and Figures.

Figure 1:
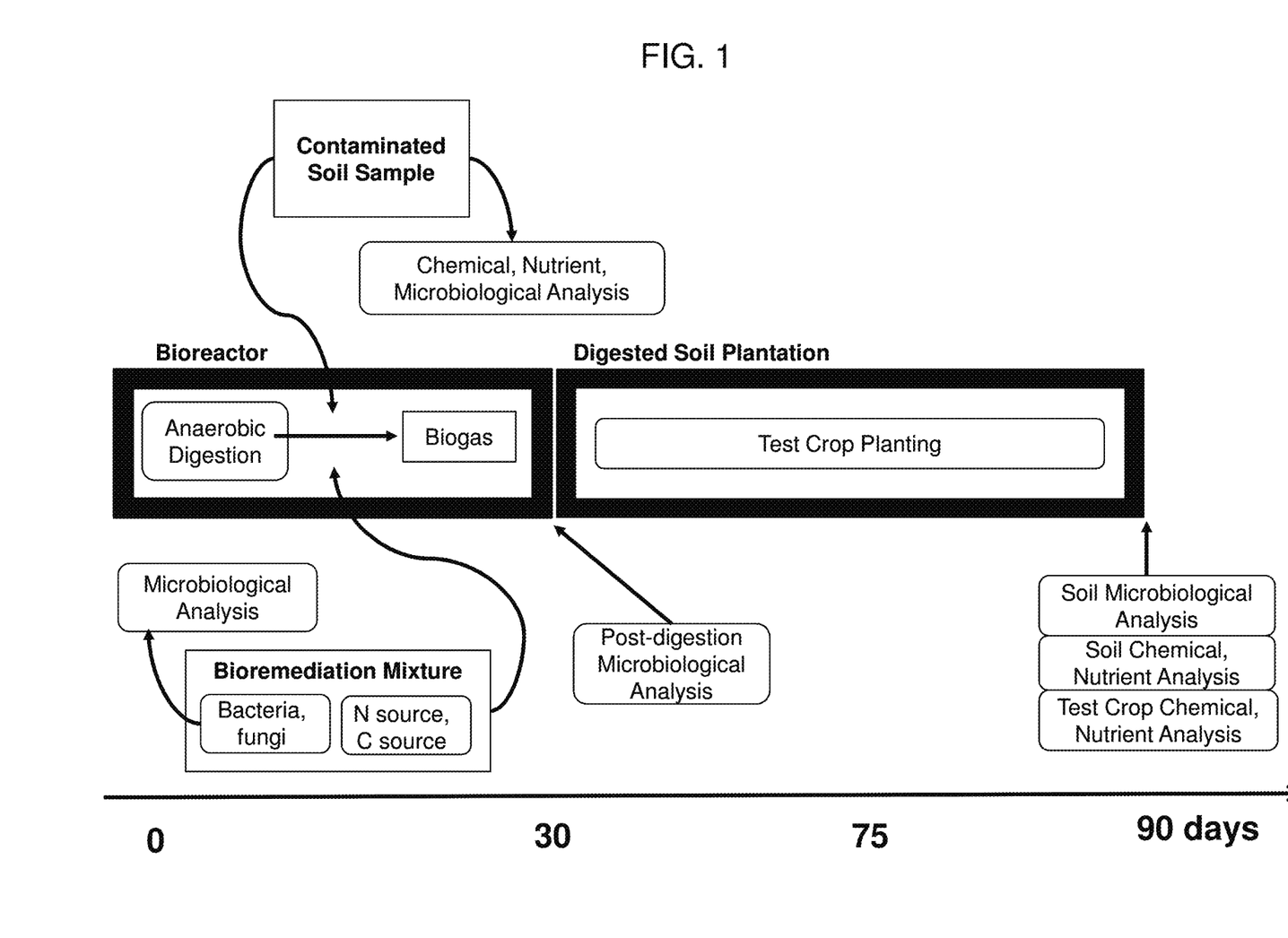
FIG. 1 shows a workflow schematic of the methods of the present disclosure that accomplish bioremediation of contaminated sludge via the use of digesters.
Figure 2:
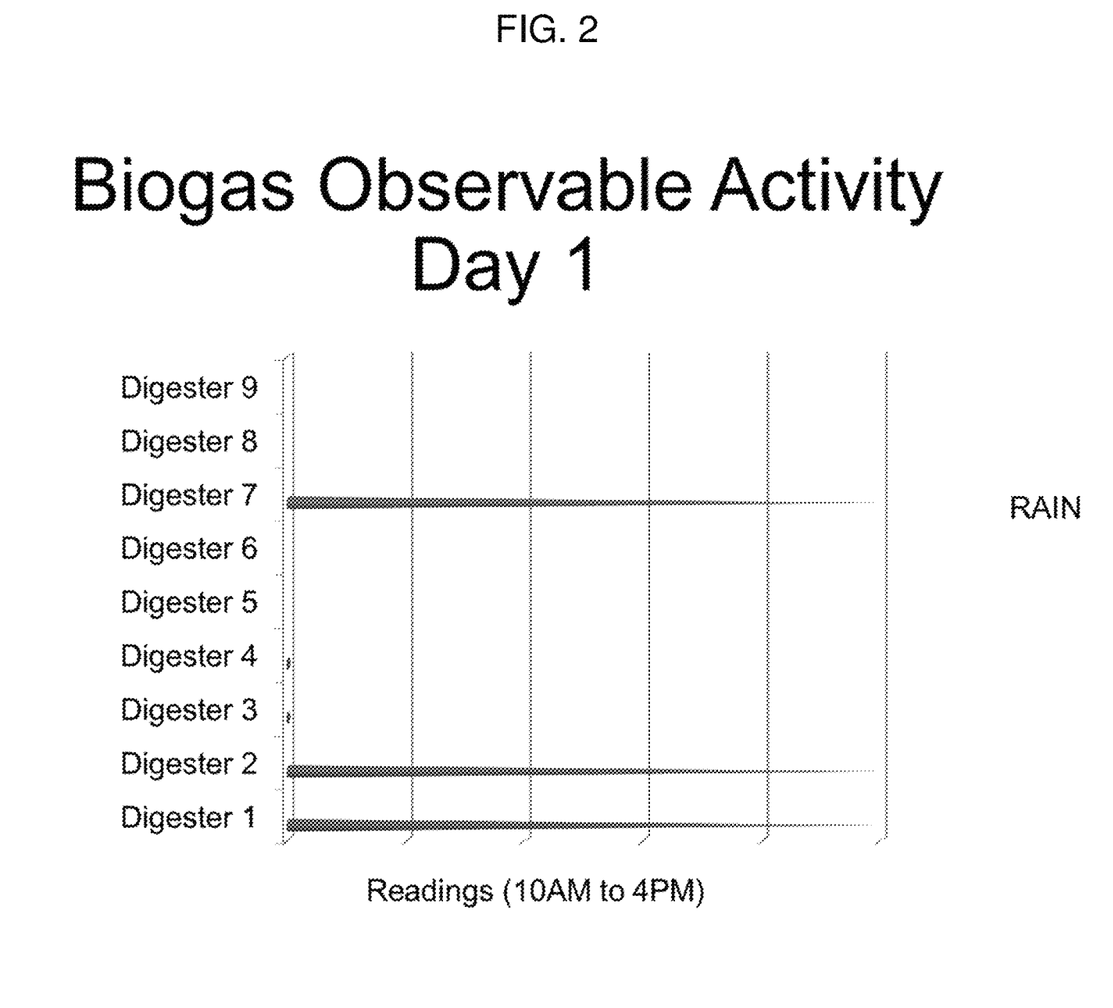
FIG. 2 shows day 1 biogas activity for digesters 1 through 9.
Figure 3:
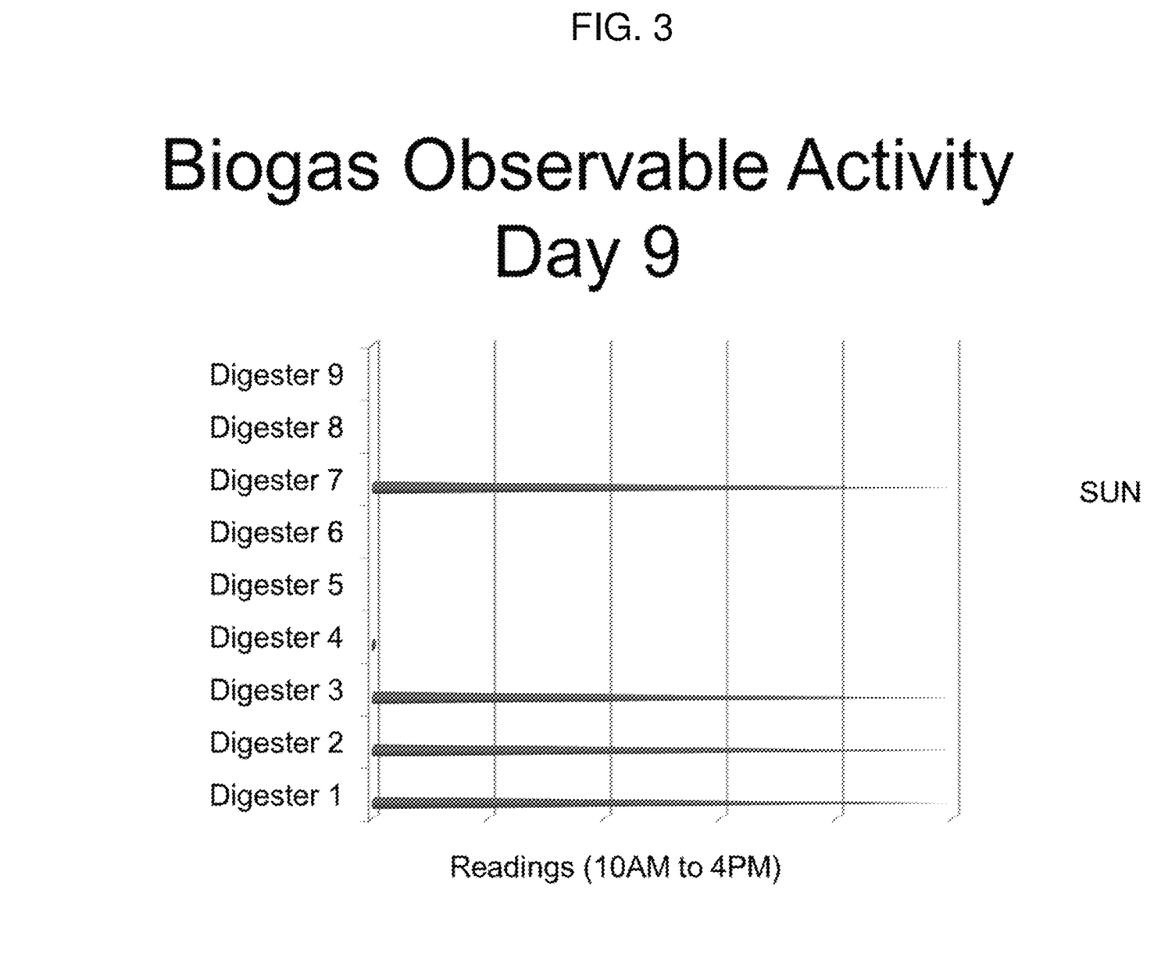
FIG. 3 shows day 9 biogas activity for digesters 1 through 9.
Figure 4:
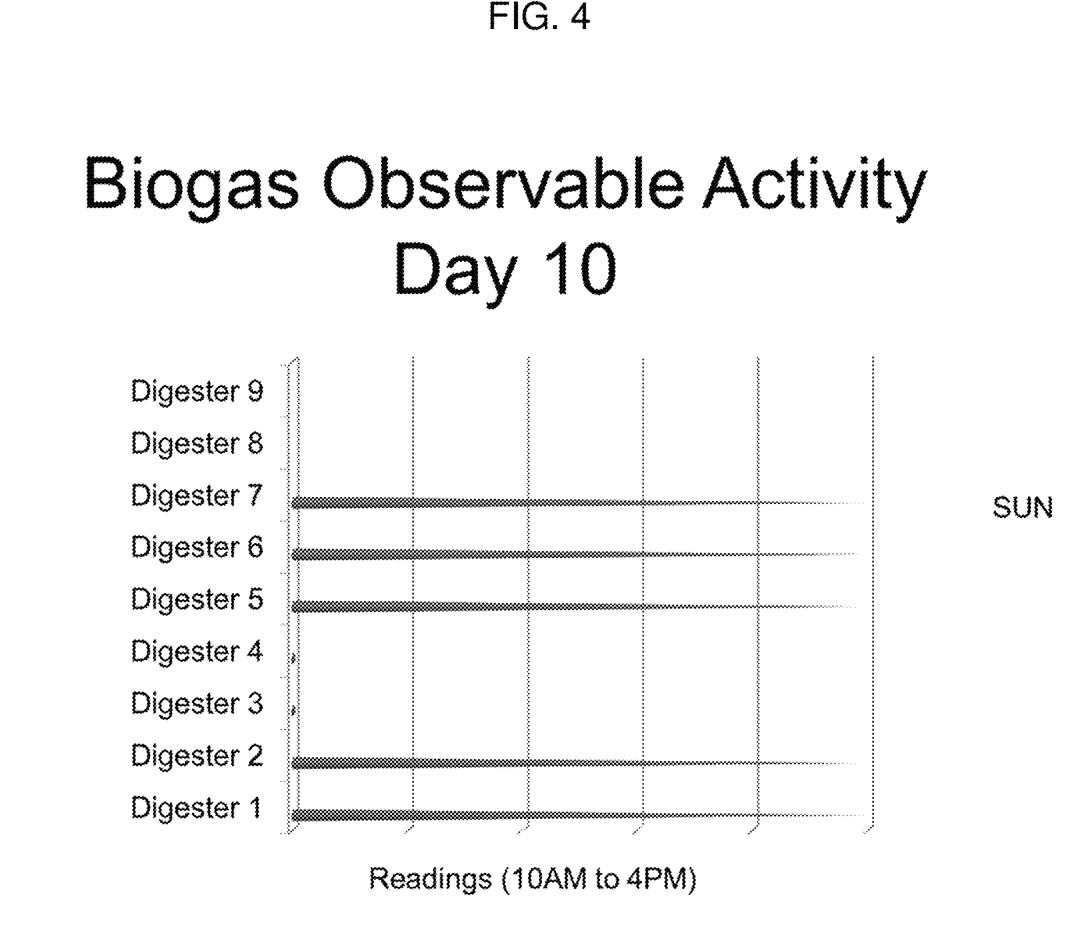
FIG. 4 shows day 10 biogas activity for digesters 1 through 9.
Figure 5:
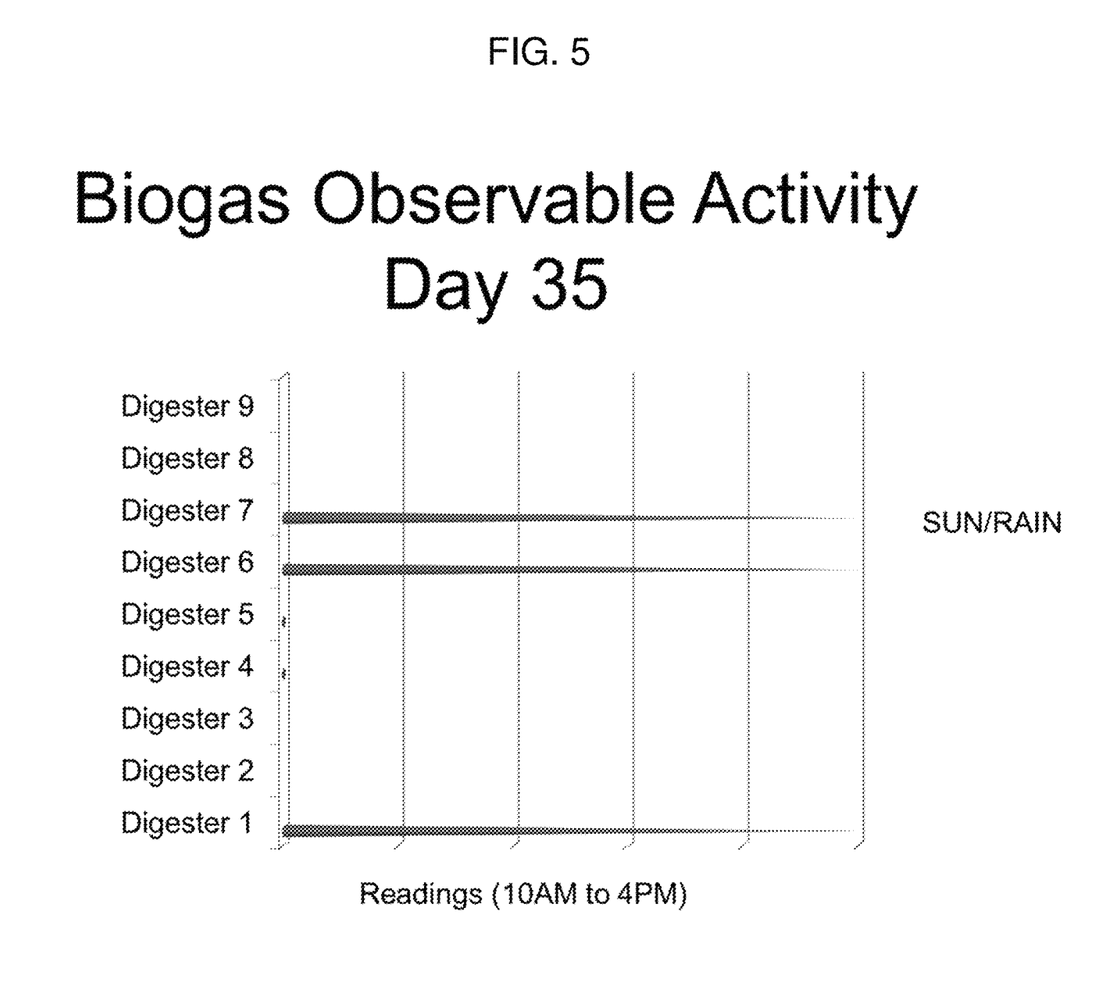
FIG. 5 shows day 35 biogas activity for digesters 1 through 9.

Embodiments of the present disclosure include methods to bioremediate heavy metals with the use of anaerobic digestion. In the instance of the Examples described below, bacteria and fungi were employed to digest soil contaminated with heavy metals (also referred to herein as "sludge") wherein the sludge was obtained from the Bento Rodrigues dam spill in Brazil. As will be seen in the Examples, detailed molecular analysis of the organisms involved in the process of metal degradation, sequestration and inactivation of the sludge were performed. In addition, chemical analysis of heavy metals, trace minerals and soil nutrients of the contaminated sludge were performed, and analysis of physical indicators of soil quality was also performed. FIG. 1 shows a workflow schematic of the methods of the present disclosure that accomplish bioremediation of contaminated sludge. The steps and components indicated in the workflow of FIG. 1 are described in greater detail below.

Chemical, Nutrient Analysis of Contaminated Soil/Sludge

Before performing the anaerobic digestion of the methods of the disclosure, a physico-chemical and nutrient analysis of the contaminated sludge was performed. The following properties were determined: soil organic matter (OM), soil pH in $H_2O$ (pH), available phosphorus (P) and potassium ($K^+$), exchangeable aluminum ($Al^{3+}$), calcium ($Ca^{2+}$) and magnesium ($Mg^{2+}$), effective cation exchange capacity (CEC) and CEC at pH 7.0, base-saturation percentage (V %) and Al saturation percentage (m %). Chemical analysis were performed according to the methods described by Tedesco et al. (Análise de solo, plantas e outros materiais. 2.ed. Porto Alegre, Universidade Federal do Rio Grande do Sul, 1995. 174p): pH measurement in water at a 1:1 soil/water ratio, extraction of exchangeable $Ca^{2+}$ and $Mg^{2+}$ with 1 mol·$L^{-1}$ KCl and determination by atomic absorption spectrophotometry. The quantity of available P and K was estimated by Mehlich-1, analyzing $K^+$ by flame photometry and P by colorimetry; extraction of exchangeable Al with 1 mol·$L^{-1}$ KCl and titration analysis with 0.0125 mol·$L^{-1}$ NaOH; and organic carbon was determined by the Walkley-Black combustion method. For OM (an indicator of nitrogen), the data of organic carbon were multiplied by 1.724. Based on the results of chemical analysis, the CEC, V % and m % were calculated. Table A shows the chemical characterization of baseline contaminated sludge for soil fertility parameters.

TABLE A

Chemical characterization of un-treated contaminated sludge and soil fertility parameters

| | | | Parameter | | | | | | | | |
|---|---|---|---|---|---|---|---|---|---|---|---|
| | OM (N) | pH ($H_2O$ 1:1) | P | $K^+$ | $Al^{3+}$ | $Ca^{2+}$ | $Mg^{2+}$ | CEC | CEC pH 7.0 | Saturation V % | M % |
| Sludge | g·$dm^{-3}$ | g·$dm^{-3}$ | mg·$dm^{-3}$ | | | cmole·$dm^{-3}$ | | | | | |
| Un-treated | 1.54 | 6.8 | 3.88 | 0.07 | 0.06 | 3.1 | 0.11 | 3.34 | 4.26 | 76.94 | 1.78 |

The total mineral constituents of soil were analyzed, namely mineral nutrients —macronutrients (P, K, Ca, Mg, B) and micronutrients (Zn, Cu, Fe, Mn)—and heavy metals (As, Ba, Cd, Co, Cr, Hg, Ni, Pb). The results are shown in Tables B and C. For the experiments the limits of quantification (LOQ) for each element were: P (39.2 mg·$Kg^{-1}$), K (5.4 mg·$Kg^{-1}$), Ca (44.4 mg·$Kg^{-1}$), Mg (15 mg·$Kg^{-1}$), B (11.2 mg·$Kg^{-1}$), Zn (3.2 mg·$Kg^{-1}$), Cu (5.4 mg·$Kg^{-1}$), Fe (4.6 mg·$Kg^{-1}$), Mn (1.4 mg·$Kg^{-1}$), As (0.05 mg·$Kg^{-1}$), Ba (1.2 mg·$Kg^{-1}$), Cd (1.2 mg·$Kg^{-1}$), Co (1.8 mg·$Kg^{-1}$), Cr (5.6 mg·$Kg^{-1}$), Hg (0.12 mg·$Kg^{-1}$), Ni (2.2 mg·$Kg^{-1}$) and Pb (17 mg·$Kg^{-1}$).

TABLE B

Total mineral nutrients in the un-treated contaminated sludge.

| | Analyte | | | | | | | | |
|---|---|---|---|---|---|---|---|---|---|
| Sludge | P | K | Ca | Mg | B | Zn | Cu | Fe | Mn |
| | | | | | mg·$Kg^{-1}$ | | | | |
| Un-treated | 872.15 | 419.64 | 1077.56 | <LOQ | <LOQ | 28.16 | <LOQ | 150714.46 | 1496.32 |

TABLE C

Total heavy metals in the un-treated contaminated sludge.

| | Analyte | | | | | | | |
|---|---|---|---|---|---|---|---|---|
| Soil | As | Ba | Cd | Co | Cr | Hg | Ni | Pb |
| | | | | | mg·$Kg^{-1}$ | | | |
| Un-treated | 6.8 | 169.6 | 96.63 | <LOQ | 31.46 | <LOQ | 151.52 | 92.33 |

Microbiological (Bacteria/Fungi) Analysis of Contaminated Soil/Sludge

Sample preparation and sequencing was performed by Neoprospecta Microbiome Technologies. Bacterial identification was performed using the V3-V4 region of rRNA 16S which was amplified with the following primers with Illumina adapters: primer 341F (CCTACGGGRSGCAGCAG) (SEQ. ID NO. 1), and primer 806R (GGACTACHVGGGTWTCTAAT) (SEQ. ID NO. 2). Fungi identification was performed using the ITS1 region with the following primers: primer ITS1 (GAACCWGCGGARGGATCA)—(SEQ. ID NO. 3), and primer ITS2 (GCTGCGTTCTTCATCGATGC)—(SEQ. ID NO. 4). Sequencing was performed by Illumina MiSeq, using a V2 kit, with a single-end 300nt run. The identification of bacterial and fungi sequences was performed using Neoprospecta proprietary database (Neopct/NeoRefDB) and the public domain GreenGenes (http://greengenes.lbl.gov).

The bioinformatics analysis was performed by Neoprospecta Microbiome Technologies. The primers and adapter sequences were trimmed from the reads, and only sequences with 275nt or more were used in downstream analysis. Then, all reads with one or more indeterminate bases "N" and truncated sequences with two or more consecutive bases with quality scores below to Q30, were eliminated. OTUs selection was performed using Blastn 2.2.28 against GreenGenes 13.8 database. Taxonomical classification was performed using stringent criteria and only for sequences with 99% identity over 99% of its length.

Surprisingly, the following most abundant microbial survivors (bacteria and fungi) were detected and were able to adapt to the noxious insults posed by heavy metal contamination (lesser abundant species not listed): uncultured bacterium, uncultured actinobacterium, uncultured *Sediminibacterium* sp., *Kaistobacter terrae*, uncultured bacterium SJA-149, uncultured delta proteobacterium, uncultured soil bacterium, *Pantoea* sp. A1133, and uncultured Acidobacteria bacterium; and fungal *Endophyte* sp. R32_3, *Clonostachys rogersoniana, Podospora communis, Clonostachys rosea F. catenulata, Fusarium* sp. FPGLXJ04, *Fusarium* sp. CS-PIF13, uncultured *Mrakia, Pisolithus tinctorius*, and fungal isolate from *Newtonia buchananii* wood. Also surprisingly, the soil directly in contact with the contaminated sludge (underneath) was found to have the following most abundant microbial survivors: uncultured bacterium, uncultured alpha proteobacterium, uncultured *Sediminibacterium* sp., *Sphingobium* sp. R8-587, *Kaistobacter terrae*, uncultured bacterium SJA-149, uncultured *Phenylobacterium* sp., uncultured soil bacterium, beta proteobacterium IMCC1729, and uncultured *Erysipeiothrix* sp.; and *Fusarium* sp. FPGLXJ04, *Cylindrocladiella pseudoparva*, fungal *endophyte, Lasiodiplodia subglobosa, Scedosporium dehoogii, Ceratobasidium* sp. AG-G, fungal sp. Griff. DX-FIR1, *Stagonospora* sp. AX113, *Bartalinia robillardoides, Podospora communis*, and *Pseudallescheria fusoidea*.

Bacteria, Fungi Cocktail & Microbiological Analysis

The initial bacterial/fungi inoculum was comprised of soil samples from 1) native forests of the States of Minas Gerais and Rio de Janeiro (cities of Bento Rodrigues and Teresópolis, respectively); 2) wood rotters from wood debris and trees, building the foundation of forest ecosystems from Bento Rodrigues and Teresópolis; 3) fungi growing on carton paper; and 4) fungi growing on wood debris that harbored termites. Table D includes the most abundant bacterial and fungi species detected in a mixture of soil samples and wood debris harboring bacteria and fungi.

These bacterial/fungi communities along with other species that were less abundant (approximately 1900 bacterial species and over 280 fungal species) made up the cocktail that was part of the bioremediation mixture and inoculated into bioreactors that performed anaerobic digestion of the contaminated sludge.

TABLE D

| | | | | |
|---|---|---|---|---|
| uncultured bacterium | 48k | *Dioszegia zsoltii* var. *zsoltii* | 1.6k |
| *Lactococcus lactis* subsp. *lactis* | 10k | uncultured soil fungus | 1.5k |
| *Chryseobacterium jejuense* | 3.5k | uncultured *Mrakia* | 1.5k |
| uncultered Acidobacteria bacterium | 2k | *Bipolaris sorakiniana* | 1.2k |
| *Pseudomonas* sp. 38_8 | 2.5k | *Epicaccum sorghinum* | 982 |
| uncultured Caulobacterales bacterium | 2k | *Pestalotiopsis coffese-arabicae* | 787 |
| uncultured organism | 1.9k | *Fusarium* sp. FPGLXJ04 | 391 |
| *Clostridium* sp. T5R32 | 1.8k | *Mucor bainieri* | 389 |
| uncultured soil bacterium | 1.8k | *Phaeosphaeria* sp. HKC12 | 370 |
| uncultured *Pantoea* sp. | 1.7k | *Trichoderma spirale* | 344 |
| uncultured alpha proteobacterium | 1.1k | *Pestalotiopsis trachicarpicola* | 291 |
| *Clostridium intestinale* | 1.1k | uncultured endophytic fungus | 267 |
| uncultured *Treponema* sp. | 1.1k | *Penicillium brevicompactum* | 236 |
| | | *Fusarium graminearum* | 222 |

Bioreactors & Bioremediation Mixtures

Nine bioreactors (also referred to herein as "biodigesters") were built to process contaminated sludge. The bioreactors were non-continuous input devices for generation of biogas and digester effluent (biofertilizer and digestate). The digester system included a bioremediation mixture which included a cocktail solution of bacteria and fungi as well as a nitrogen source and a carbon source for anaerobic digestion. The residence period (retention time) was 35 days for the following examples, however the residence period could be any number of days in the range of from 5 days to 35 days. For example, if heat were applied to a bioreactor, the number of days could be as low as 5, 6 or 7 days, for instance. If no heat were applied to a bioreactor, the number of days could be as high as 28 to 35 days, for instance. Examples 1 to 9 show the composition and constituents of the nine bioreactors.

Example 1

| Bioreactor 1 (80 L) | |
|---|---|
| component | Qty |
| Microbiome/Virome Complex Solution (batch of 5.2 L bacteria/fungi in 70 L water) | 8 L |
| Contaminated Sludge | 20 L |
| Sources of Nitrogen | |
| fish | 7.5 L |
| Sources of Carbon | |
| ash | 100 g |
| trumpetwood | 2-3 flowers |
| sugarcane bagasse | 200 g |
| *Brachiaria* grass | 400 g |
| bamboo | 400 g |
| sawdust | 800 g |

Biogas production was observed and documented on a daily basis for the residence period (35 days) (see FIGS. 2-5). After anaerobic digestion of the contaminated sludge by the noted components, the most abundant bacterial and fungi species for the biofertilizer (the liquid) were determined to be: uncultured bacterium, *Bacteroides coprasuis* DSM 18011, uncultured prokaryote, *Sparanaerobacter* sp.

SN 28, swine effluent bacterium, *Lysobacter* sp. RB-3 1, bacterium NLAE-z1-P83, uncultured compost bacterium, bacterium NLAE-z1-C230 and uncultured *Caloramator* sp. for bacteria; and *Podospora decipiens, Podospora communis, Fusarium* sp. mcp0910, *Pseudallescheria fusoidea*, uncultured soil fungus, *Chaetomium globosum*, fungal sp. Griff. DX-FIR1, *Penicillium mononematosum, Penicillium vanluykii* and *Saccharomyces serevisiae* for fungi.

In addition, the most abundant bacterial and fungi species for the digestate (the solids) present in the bioreactor were determined to be: bacterium NLAE-z1-C230, bacterium NLAE-a1-P83, *Bacteroides coprosuis* DSM 18011, *Methanofollis* sp. YCM4, *Sporanaerobacter* sp. SN28, swine effluent bacterium CHNDP11, uncultured bacterium, uncultured *Caloramator* sp., uncultured compost bacterium and uncultured prokaryote for bacteria; and *Chaetomium globosum, Coprinopsis calospora*, fungal sp. 2686 YZ-2011, fungal sp. Griff. DX-FIR1, *Ganoderma annulare, Geomyces* sp. 12NJ08, *Periconia* sp. CY137, *Phaeosphaeria* sp. HKC12, *Podospora communis* and *Scedosporium dehoogii* for fungi.

Example 2

| Bioreactor 2 (80 L) | |
|---|---|
| component | Qty |
| Microbiome/Virome Complex Solution (batch of 5.2 L bacteria/fungi in 70 L water) | 8 L |
| Contaminated Sludge | 20 L |
| Sources of Nitrogen | |
| fish | 7.5 L |
| sugar cane juice | 1 L |
| Sources of Carbon | |
| ash | 100 g |
| trumpetwood | 2-3 flowers |
| sugarcane bagasse | 200 g |
| *Brachiaria* grass | 400 g |
| bamboo | 400 g |
| sawdust | 800 g |

Biogas production was observed and documented on a daily basis for the residence period (35 days) (see FIGS. 2-5). After anaerobic digestion of the contaminated sludge by the noted components, the most abundant bacterial and fungi species for the biofertilizer (the liquid) were determined to be: uncultured bacterium, uncultured compost bacterium, bacterium NLAE-z1-P83, swine effluent bacterium CHNDP11, bacterium NLAE-z1-C230, *Clostridium botulinum* C str. Eklund, *Sparanaerobacter* sp. SN 28, uncultured *Caloramator* sp., *Bacteroides coprasuis* DSM 18011, and *Acetobacter ghanensis* for bacteria; and fungal sp. Griff. DX-FIR1 and *Humicola fuscoatra* for fungi.

In addition, the most abundant bacterial and fungi species for the digestate (the solids) present in the bioreactor were determined to be: *Bacillus* sp. SL168, bacterium NLAE-z1-C230, bacterium NLAE-z1-P83, *Bacteroides coprosuis* DSM 18011, *Lactobacillus acidipiscis*, swine effluent bacterium CHNDP11, uncultured bacterium, uncultured Bacteroidetes bacterium, uncultured *Caloramator* sp. And uncultured prokaryote for bacteria; and *Cladosporium halotolerans, Clonostachys rogersoniana, Epicoccum sorghinum*, fungal sp. 2686 YZ-2011, fungal sp. Griff. DX-FIR1, *Meyerazyma caribbica, Mortierella exigua, Phaeosphaeria* sp. HKC12*, Preussia* sp. BSH2.9 and *Scedosporium dehoogii* for fungi.

Example 3

| Bioreactor 3 (80 L) | |
|---|---|
| component | Qty |
| Microbiome/Virome Complex Solution (batch of 5.2 L bacteria/fungi in 70 L water) | 8 L |
| Contaminated Sludge | 20 L |
| Sources of Nitrogen | |
| cow dung | 3 L |
| fish | 3 L |
| Sources of Carbon | |
| ash | 100 g |
| trumpetwood | 2-3 flowers |
| sugarcane bagasse | 200 g |
| *Brachiaria* grass | 400 g |
| bamboo | 400 g |
| sawdust | 800 g |

Biogas production was observed and documented on a daily basis for the residence period (35 days) (see FIGS. 2-5). After anaerobic digestion of the contaminated sludge by the noted components, the most abundant bacterial and fungi species for the biofertilizer (the liquid) were determined to be: uncultured bacterium, *Methanocorpusculum labreanum* Z, *Arcobacter skirrowii* CCUG 10374, bacterium SM-5-6, bacterium enrichment culture clone PA4, *Arthrobacter* sp. PD9*, Petrimonas sulfuriphila*, uncultured *Clostridiaceae bacterium*, archaeo n PY-12 and uncultured anaerobic bacterium for bacteria; and *Podospora communis*, fungal sp. Griff. DX-FIR1, *Saccharomyces cerevisiae*, fungal sp. 2686 YZ-2011*, Montagnulaceae* sp. MM 6_1_a, *Mortierella lignicola* and uncultured *Chaetomiaceae* for fungi.

In addition, the most abundant bacterial and fungi species for the digestate (the solids) present in the bioreactor were determined to be: *Arcobacter butzleri* ED-1, *Arthrobacter* sp. PD9, *Bacteroides paurosaccharolyticus, Methanocorpusculum labreanum* Z, *Petrimonas sulfuriphila*, uncultured *Aquabacterium* sp., uncultured bacterium, uncultured Bacteroidetes bacterium, uncultured *Lysinibacillus* sp. and uncultured soil bacterium for bacteria; and *Aspergillus* sp. F55, *Cladosporium halotolerans, Epicaccum sorghinum*, fungal sp. Griff. DX-FIR1*, Geomyces* sp. 12NJ08*, Podospora decipiens, Preussia terricola* and *Zygosaccharomyces rouxii* for fungi.

Example 4

| Bioreactor 4 (80 L) | |
|---|---|
| Component | Qty |
| Microbiome/Virome Complex Solution (batch of 5.2 L bacteria/fungi in 70 L water) | 8 L |
| Contaminated Sludge | 20 L |
| Sources of Nitrogen | |
| cow dung | 3 L |
| fish | 3 L |
| sugar cane juice | ½ L |
| Sources of Carbon | |
| ash | 100 g |
| trumpetwood | 200 g |
| sugarcane bagasse | 200 g |
| *Brachiaria* grass | 400 g |

-continued

| Bioreactor 4 (80 L) | |
|---|---|
| Component | Qty |
| bamboo | 400 g |
| sawdust | 800 g |

Biogas production was observed and documented on a daily basis for the residence period (35 days) (see FIGS. 2-5). After anaerobic digestion of the contaminated sludge by the noted components, the most abundant bacterial and fungi species for the biofertilizer (the liquid) were determined to be: uncultured bacterium, *Arcobacter thereius* LMG 24486, *Arthrobacter* sp. PD9, *Methanocorpusculum labreanum* Z, *Arcobacter skirrowii* CCUG 10374, uncultured *Alcaligenes* sp., *Myroides [odoratimimus]* CIP 103059, *Petrimonas sulfuriphila*, *Pseudomonas* sp. SKU, and bacterium SM-5-6 for bacteria; and fungal sp. AM2013, *Podospora decipiens, Fusarium* sp. FPGLXJ04, *Saccharoinyces cerevisiae, Preussia* sp. JJP-2009a, fungal sp. 2686 YZ-2011, *Meyerozyma caribbica, Chaetomium globosum, Migrospora oryzae, Podospora communis* and uncultured fungus for fungi.

In addition, the most abundant bacterial and fungi species for the digestate (the solids) present in the bioreactor were determined to be: bacterium NLAE-z1-C156, *Bacteroides coprosuis* DSM 18011, *Bacteroides graminisolvens, Bacteroides paurosaccharalyticus*, iron-reducing bacterium enrichment culture clone HN-HF012, *Petrimonas sulfuriphila*, uncultured *Anaerofilum* sp., uncultured archaean, uncultured bacterium and uncultured Bacteroidetes bacterium for bacteria; and fungal sp. 2686 YZ-2011, fungal sp. Griff. DX-FIR1, *Orpinomyces* sp. NIANP57, *Pleosporales* sp. PANB1a0818P30CC484, *Podospora communis, Podospora decipiens, Preussia* sp. BSH2.9, *Scedosporium dehoogii* and uncultured *Orpinomyces* for fungi.

Example 5

| Bioreactor 5 (80 L) | |
|---|---|
| component | Qty |
| Microbiome/Virome Complex Solution (batch of 5.2 L bacteria/fungi in 70 L water) | 8 L |
| Contaminated Sludge | 20 L |
| Sources of Nitrogen | |
| cow dung | 3 L |
| sugar cane juice | 1 L |
| Sources of Carbon | |
| ash | 100 g |
| trumpetwood | 2-3 flowers |
| sugarcane bagasse | 200 g |
| *Brachiaria* grass | 400 g |
| bamboo | 400 g |
| sawdust | 800 g |

Biogas production was observed and documented on a daily basis for the residence period (35 days) (see FIGS. 2-5). After anaerobic digestion of the contaminated sludge by the noted components, the most abundant bacterial and fungi species for the biofertilizer (the liquid) were determined to be: uncultured bacterium, *Methanocorpusculum labreanum* Z, uncultured soil bacterium, *Bacteroides paurosaccharolycicus, Lysobacter brunescens*, uncultured *Aquabacterium* sp., uncultured *Flavobacterium* sp., *Petrimonas sulfuriphila*, uncultured Bacteroidetes bacterium and *Bacteroides graminisavens* for bacteria; and *Papulaspora equi, Podospora communis*, fungal sp. 2686 YZ-2011, *Podospora decipiens, Wickerhamomyces anomalus*, fungal sp. AM2013, *Humicola fuscoatra, Preussia* sp. JJP-2009a, *Scedosporium apiospermum, Scedosporium dehoogil, Thermomyces lanuginosus* and *Zygosaccharoinyces rouxil* for fungi.

In addition, the most abundant bacterial and fungi species for the digestate (the solids) present in the bioreactor were determined to be: bacterium enrichment culture clone Ecwsrb0, *Bacteroides graminisolvens, Bacteroides paurosaccharolyticus, Methanocorpusculum labreanum* Z, *Petrimonas sulfuriphila*, uncultured bacterium, uncultured Bacteroidetes bacterium, uncultured Porphyromonadaceae bacterium, uncultured soil bacterium and uncultured spirochete for bacteria; and *Ceriporia melfea, Coprinellus brevisetulosus*, fungal sp. Griff. DX-FIR1, *Meyerozyma caribbica, nigrospora* sp. TSS-151, *Nigrospora sphaerica, Ogataea polymorpha, Orpinomyces* sp. NIANP57, *Podospora communis, Preussia* sp. BSH2.9, *Saccharomyces cerevisiae, Scedosporium apiospemum, Zygosaccharomyces rouxii* and uncultured *Orpinomyces* for fungi.

Example 6

| Bioreactor 6 (120 L) | |
|---|---|
| component | Qty |
| Microbiome/Virome Complex Solution (batch of 5.2 L bacteria/fungi in 70 L water) | 12 L |
| Contaminated Sludge | 20-30 L |
| Sources of Nitrogen | |
| cow dung | 10 L |
| Sources of Carbon | |
| ash | 200 g |
| trumpetwood | 2-3 flowers |
| sugarcane bagasse | 400 g |
| *Brachiaria* grass | 600 g |
| bamboo | 600 g |
| sawdust | 1.2 kg |

Biogas production was observed and documented on a daily basis for the residence period (35 days) (see FIGS. 2-5). After anaerobic digestion of the contaminated sludge by the noted components, the most abundant bacterial and fungi species for the biofertilizer (the liquid) were determined to be: uncultured bacterium, *Methanocorpusculum labreanum* Z, *Wolinella succinogenes* DSM 1740, *Bacteroides graminisolvens*, uncultured Bacteroidetes bacterium, *Sulfurospirillum deleyianum* DSM 6946, bacterium enrichment culture clone PA4, *Flavobacterium suncheonense, Pseudomonas* sp. C1(2011) and uncultured compost bacterium for bacteria; and *Podospora communis, Epicoccum sorghinum, Podospora decipiens*, fungal sp. AM2013, *Phoma paspali, Lectera colletotrichoides, Byssochlamys spectabilis, Meyerozyma caribbica* and *Saccharomyces cerevisiae* for fungi.

In addition, the most abundant bacterial and fungi species for the digestate (the solids) present in the bioreactor were determined to be: *Azonexus caeni*, bacterium enrichment culture clone PA4, *Desulfomicrobium baculatum* DSM 4028, *Methanocorpusculum labreanum* Z, *Petrimonas sulfuriphila, Pseudomonas* sp. C1(2011), uncultured anaerobic bacterium, uncultured bacterium, uncultured Bacteroidetes bacterium and uncultured soil bacterium for bacteria; and *Bartalinia robillardoides, Cryptococcus adeliensis, Epicoccum sorghinum,* fungal sp. 2686 YZ-2011, *Fusarium* sp. FPGLXJ04, *Lectera colletotrichoides, Lomentospora prolifican, Phaeosphaeria* sp. HKC12, *Pleosporales* sp. PANB1a0818P30CC484, *Podospora communis, Preussia* sp. JJP-2009a, *Saccharomyces cerevisiae, Sordaria* sp. SS-1479, *Thelonectria rubi, Trichoderma* sp. HV-2014p, uncultured endophytic fungus and uncultured Ramularia for fungi.

Example 7

| Bioreactor 7 (120 L) | |
|---|---|
| component | Qty |
| Microbiome/Virome Complex Solution (batch of 5.2 L bacteria/fungi in 70 L water) | 12 L |
| Contaminated Sludge | 20-30 L |
| Sources of Nitrogen | |
| sugar cane juice | 1.5 L |
| Sources of Carbon | |
| ash | 200 g |
| trumpetwood | 2-3 flowers |
| sugarcane bagasse | 400 g |
| *Brachiaria* grass | 600 g |
| bamboo | 600 g |
| sawdust | 1.2 kg |

Biogas production was observed and documented on a daily basis for the residence period (35 days) (see FIGS. 2-5). After anaerobic digestion of the contaminated sludge by the noted components, the most abundant bacterial and fungi species for the biofertilizer (the liquid) were determined to be: uncultured bacterium, *Lactobacillus uvarum*, uncultured Bacteroidetes bacterium, *Bacteroides graminisolvens, Pseudomonas* sp. NTUIOB TPZ, uncultured *Acidovorax* sp., *Brevundimonas* sp. HINF004, *Pedobacter composti*, bacterium NLAE-Z1-C156, *Novosphingobium aromaticivorans* DSM 12444 and uncultured *Aquabacterium* sp. for bacteria; and fungal sp. Griff. DX-FIR1 for fungi.

In addition, the most abundant bacterial and fungi species for the digestate (the solids) present in the bioreactor were determined to be: *Bacteroides graminisolvens, Clostridium* sp. 6-44, *Desulfitobacterium* sp. Enrichment culture clone AusD, *Ilyobacter delafieldii, Petrimonas sulfuriphila, Rummeliibacillus pycnus,* uncultured bacterium, uncultured *Bacteroides* sp., uncultured Bacteroidetes bacterium, uncultured *Campylobacter* sp. And uncultured *Lysinibacillus* sp. for bacteria; and fungal sp. Griff. DX-FIR1, *Meyerozyma caribbica, Podospora communis, Rhodotorula mucilaginosa, Saccharomyces cerevisiae, Scedosporium apiospermum* and *Scedosporium dehoogii* for fungi.

Example 8

| Bioreactor 8 (120 L) | |
|---|---|
| component | Qty |
| Microbiome/Virome Complex Solution (batch of 5.2 L bacteria/fungi in 70 L water) | 12 L |
| Contaminated Sludge | 20-30 L |
| Sources of Nitrogen | |
| sugar cane juice | ¼ L |
| cow dung | 7 L |
| Sources of Carbon | |
| *Lithothamnium calcareum* | 200 g |
| trumpet wood | 2-3 flowers |
| sugarcane bagasse | 400 g |
| *Brachiaria* grass | 600 g |
| bamboo | 600 g |
| sawdust | 1.2 kg |

Biogas production was observed and documented on a daily basis for the residence period (35 days) (see FIGS. 2-5). After anaerobic digestion of the contaminated sludge by the noted components, the most abundant bacterial and fungi species for the biofertilizer (the liquid) were determined to be: uncultured bacterium, *Lysobacter brunescens, Magnetospirillum aberrantis, Methanocorpusculum labreanum Z, Azospirillum thiophilum,* uncultured Bacteroidetes bacterium, bacterium enrichment culture clone PA4, *Azonexus caeni, Pedobacter composti* and uncultured soil bacterium for bacteria; and *Pseudallescheria fusoidea, Scedosporium dehoogii,* fungal sp. 2686 YZ-2011, *Fusarium* sp. CS-P/F13, *Fusarium* sp. FPGLXJ04, *Scedosporium boydii, Pestalotiopsis* coffeae-arabicae, *Preussia* sp. BSH2.9, *Saccharomyces cerevisiae,* basidiomycete sp. S22849, *Panaeolus* sp. MW-2010, *Pleosporales* sp. PANB1a0818P30CC404 and *Trichoderma koningiopsis* for fungi.

In addition, the most abundant bacterial and fungi species for the digestate (the solids) present in the bioreactor were determined to be: *Brevundimonas viscosa, Kaistobacter terrae, Lacibacter cauensis, Novosphingobium* sp. SaMRH4, *Pseudomonas* sp. NTUIOB TPZ, *Salimonas flava,* uncultured bacterium, uncultured *Sediminibacterium* sp., uncultured soil bacterium and uncultured Xanthomonadaceae bacterium for bacteria; and *Cercospora olivascens, Exophiala cancerae, Fonsecaea brasiliensis,* fungal sp. 2686 YX-2011, *Fusarium* sp. CS-P/F13, *Fusarium* sp. FPGLXJ04, *Fusarium* sp. Mcp0910, *Podospora communis, Pseudallescheria fusoidea, Scedosporium dehoogii* and *Zygosaccharomyces rouxii* for fungi.

Example 9

| Bioreactor 9 (120 L) | |
|---|---|
| component | Qty |
| Microbiome/Virome Complex Solution (batch of 5.2 L bacteria/fungi in 70 L water) | 12 L |
| Contaminated Sludge | 20-30 L |
| Sources of Nitrogen | |
| sugar cane juice | ¼ L |
| cow dung | 7.5 L |

-continued

Bioreactor 9 (120 L)

| component | Qty |
|---|---|
| Sources of Carbon | |
| ash | 200 g |
| trumpetwood | 2-3 flowers |
| sugarcane bagasse | 400 g |
| *Brachiaria* grass | 600 g |
| bamboo | 600 g |
| sawdust | 1.2 kg |

Biogas production was observed and documented on a daily basis for the residence period (35 days) (see FIGS. 2-5). After anaerobic digestion of the contaminated sludge by the noted components, the most abundant bacterial and fungi species for the biofertilizer (the liquid) were determined to be: uncultured bacterium, *Methanocorpusculum labreanum* Z, uncultured *Trichococcus* sp., *Sedimentibacter* sp. B4, uncultured Bacteroidetes bacterium, bacterium enrichment culture clone PA4, uncultured soil bacterium, uncultured Acidobacteria bacterium, *Azonexus caeni* and *Petrlinonas sulfuriphila* for bacteria; and uncultured soil fungus, fungal sp. 2686 YZ-2011, *Scedosporium dehoogii*, *Fusarium* sp. FPGLXJ04, *Mortierella exigua*, *Geomyces* sp. 12NJ08, *Podospora communis*, *Clitopilus scyphoides* and *Sordaria* sp. SS-1479 for fungi.

In addition, the most abundant bacterial and fungi species for the digestate (the solids) present in the bioreactor were determined to be: *Bradyrhizobium* sp. RITF 522, uncultured Acidobacteria bacterium, uncultured alpha proteobacterium, uncultured bacterium, uncultured Bacteroidetes bacterium, uncultured Chloroflexi bacterium, uncultured *Kaistobacter* sp., uncultured proteobacterium, uncultured soil bacterium and uncultured Sphingomonadaceae bacterium for bacteria; and fungal endophyte, fungal sp. 2686 YZ-2011, *Fusarium acutatum*, *Fusarium* sp. FPGLXJ04, *Geomyces* sp. 12NJ08, *Mortierella amoeboidea*, *Mortierella exigua*, *Mucor racemosus* F. *racemosus*, *Scedosporium dehoogii* and uncultured soil fungus for fungi.

Biogas

As can be seen from FIGS. 2-5 for Examples/Bioreactors 1-9, a compilation of best performers in terms of biogas production over the period of 35 days indicated in descending order that digester 1 (20 days), digester 6 (16 days), digester 2 (14 days), digester 7 (10 days), digester 3 (4 days) and digester 5 (4 days) exhibited best output of biogas. Notably, some of the digesters were still producing biogas at day 35 (see FIG. 5).

Digested Soil Plantation

Figure 6:
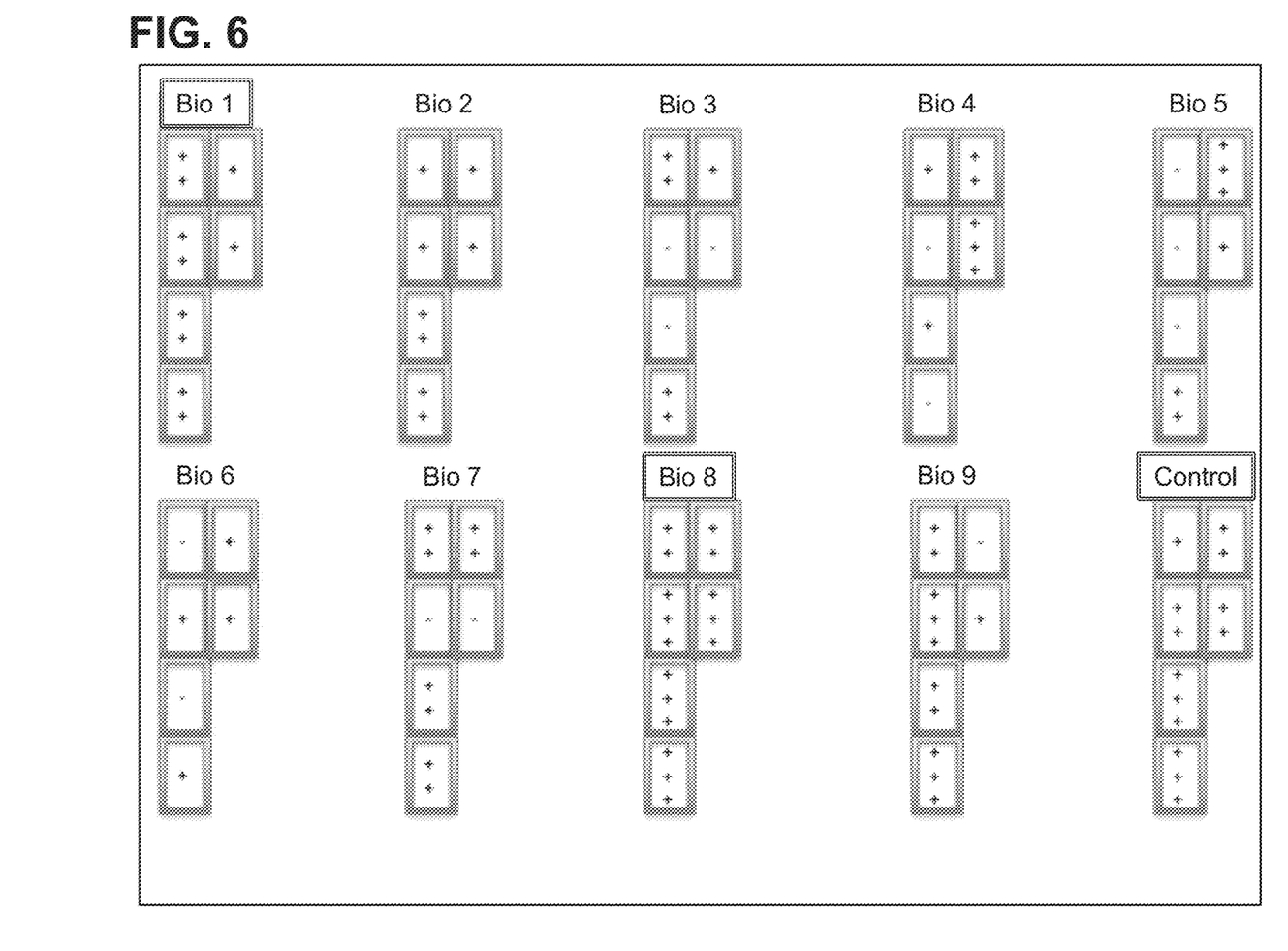
FIG. 6 includes a table showing the results of the best plant beds based on plant height attributes.

The digestate obtained from a given bioreactor was used as an indicator of soil suitability for plantation of test crops, for example crotalaria and corn. *Crotalaria* and corn seeding was performed in quadruplicate for each bioreactor. In addition, existing soil from a field laboratory was used as an additional control. Sixty-days after the end of anaerobic digestion and the start of soil plantation, plant height was deemed as an indicator of soil quality. It is noted here that the sixty days may be altered to a number of days with a range of from 45 to 75 days. FIG. 6 includes a table showing the results of the best plant beds based on plant height attributes.

It can be seen from Table E that the best indicators of soil quality were bioreactors 1 and 8 and the control. Bioreactor 8 was deemed the best among the three best. Notably, this was the only bioreactor that had *Lithothamnium calcareum* (a red marine algae) in its bioremediation mixture.

Test Crop and Soil Chemical, Nutrient Analysis & Soil Microbiological Analysis

Soil chemical analysis was performed to check the efficiency of the biodigestion process. Table F shows the chemical characterization of the untreated soil and the results of the 9 biodigesters (1 to 9) and a control (10) for soil fertility parameters. The following properties were determined: soil organic matter (OM), soil pH in $H_2O$ (pH), available phosphorus (P) and potassium ($K^+$), exchangeable aluminum ($Al^{3+}$), calcium ($Ca^{2+}$) and magnesium ($Mg^{2+}$), effective cation exchange capacity (CEC) and CEC at pH 7.0, base-saturation percentage (V %) and Al saturation percentage (m %). Chemical analysis was performed according to the methods described by Tedesco et al. (1995): pH measurement in water at a 1:1 soil/water ratio, extraction of exchangeable $Ca^{2+}$ and $Mg^{2+}$ with 1 mol·$L^{-1}$ KCl and determination by atomic absorption spectrophotometry. The quantity of available P and K was estimated by Mehlich-1, analyzing $K^+$ by flame photometry and P by colorimetry; extraction of exchangeable Al with 1 mol·$L^{-1}$ KCl and titration analysis with 0.0125 mol·$L^{-1}$ NaOH; and organic carbon was determined by the Walkley-Black combustion method. For OM, the data of organic carbon were multiplied by 1.724. Based on the results of chemical analysis, the CEC, V % and m % were calculated.

TABLE F

Chemical characterization of un-treated and post-treated soil (soil 1 to 10) from soil fertility parameters

| | | Parameter | | | | | | | | | |
|---|---|---|---|---|---|---|---|---|---|---|---|
| | OM | pH (H2O 1:1) | P | | | | | CEC | | Saturation | |
| Soil | g·$dm^{-3}$ | g·$dm^{-3}$ | mg·$dm^{-3}$ | $K^+$ | $Al^{3+}$ | $Ca^{2+}$ | $Mg^{2+}$ cmole·$dm^{-3}$ | CEC | pH 7.0 | V % | M |
| Untreated | 1.54 | 6.8 | 3.88 | 0.07 | 0.06 | 3.1 | 0.11 | 3.34 | 4.26 | 76.94 | 1.78 |
| 1 | 4.69 | 6 | 127.84 | 0.18 | 0.00 | 9.92 | 1.16 | 11.26 | 13.45 | 83.73 | 0.00 |
| 2 | 2.69 | 6.2 | 47.16 | 0.15 | 0.00 | 7.45 | 0.67 | 8.27 | 10.01 | 82.62 | 0.00 |
| 3 | 4.56 | 6.1 | 102.73 | 0.30 | 0.00 | 9.22 | 1.06 | 10.58 | 13.04 | 81.16 | 0.00 |
| 4 | 3.69 | 6.2 | 81.36 | 0.30 | 0.00 | 8.74 | 1.03 | 10.07 | 12.82 | 78.52 | 0.00 |
| 5 | 4.88 | 6.3 | 83.30 | 0.20 | 0.00 | 9.63 | 1.39 | 11.21 | 13.66 | 82.03 | 0.00 |
| 6 | 3.69 | 6.4 | 98.98 | 0.83 | 0.00 | 8.82 | 1.20 | 10.85 | 12.40 | 87.49 | 0.00 |
| 7 | 2.86 | 6.3 | 76.25 | 0.15 | 0.00 | 8.56 | 0.90 | 9.61 | 11.56 | 83.12 | 0.00 |

TABLE F-continued

Chemical characterization of un-treated and post-treated soil (soil 1 to 10) from soil fertility parameters

| | | Parameter | | | | | | | | | |
|---|---|---|---|---|---|---|---|---|---|---|---|
| | OM | pH (H2O 1:1) | P | | | | | | CEC | Saturation | |
| Soil | g·dm$^{-3}$ | g·dm$^{-3}$ | mg·dm$^{-3}$ | K$^+$ | Al$^{3+}$ | Ca$^{2+}$ | Mg$^{2+}$ cmole·dm$^{-3}$ | CEC | pH 7.0 | V % | M |
| 8 | 2.98 | 6.1 | 62.50 | 0.31 | 0.00 | 8.03 | 1.04 | 9.38 | 11.33 | 82.77 | 0.00 |
| 9 | 2.43 | 6.1 | 56.59 | 0.21 | 0.00 | 8.19 | 0.92 | 9.32 | 11.51 | 80.98 | 0.00 |
| 10 | 2.69 | 6.3 | 97.16 | 0.44 | 0.00 | 9.72 | 1.32 | 11.47 | 14.56 | 78.78 | 0.00 |

Generally, the results in Table F show an increase in soil fertility after the biodigestion process, with variations according to biodigester. An improvement was observed in the levels of organic matter from low to medium or good. The untreated soil showed a high pH value, and post-treated soil exhibited pH values considered acceptable for agronomic purposes. With respect to available phosphorus (P) and potassium (K), the P levels increased to very good levels (>45 mg·dm$^{-3}$) in all treated soils, while there was an increase in the content of exchangeable potassium in all treated soil. The ion exchange capacity (CEC) of the soil is the gradual release capacity of various nutrients, favoring the maintenance of fertility for a long time. A good soil for agronomic purposes presented effective CEC occupied by essential cations such as Ca$^{2+}$, Mg$^{2+}$ and K$^+$ as it was observed in treated soils (1 to 10). On the other hand, in a poor soil the effective CEC is occupied by potentially toxic cations such as Al$^{3+}$ and it has a low value of CEC indicating that the soil has small capacity to retain cations in exchangeable form. The base saturation (V %) is an excellent indicator of the general conditions of soil fertility, and high values of V % represent fertile soil. A good productivity was observed for the great majority of cultures when the soil has a V % value between 50-80% and a pH value between 6.0-6.5.

The total mineral constituents of soil were also analyzed, namely mineral nutrients —macronutrients (P, K, Ca, Mg, B) and micronutrients (Zn, Cu, Fe, Mn)—and heavy metals (As, Ba, Cd, Co, Cr, Hg, Ni, Pb). The results are shown in Tables G and H. For the experiments, the limits of quantification (LOQ) for each element were: P (39.2 mg·Kg$^{-1}$), K (5.4 mg·Kg$^{-1}$), Ca (44.4 mg·Kg$^{-1}$), Mg (15 mg·Kg$^{-1}$), B (11.2 mg·Kg$^{-1}$), Zn (3.2 mg·Kg$^{-1}$), Cu (5.4 mg·Kg$^{-1}$), Fe (4.6 mg·Kg$^{-1}$), Mn (1.4 mg·Kg$^{-1}$), As (0.05 mg·Kg$^{-1}$), Ba (1.2 mg·Kg$^{-1}$), Cd (1.2 mg·Kg$^{-1}$), Co (1.8 mg·Kg$^{-1}$), Cr (5.6 mg·Kg$^{-1}$), Hg (0.12 mg·Kg$^{-1}$), Ni (2.2 mg·Kg$^{-1}$) and Pb (17 mg·Kg$^{-1}$).

TABLE G

Total mineral nutrients in the untreated and post-treated soil (soil 1 to 10).

| Soil | P | K | Ca | Mg | B | Zn | Cu | Fe | Mn |
|---|---|---|---|---|---|---|---|---|---|
| | | | | | mg·Kg$^{-1}$ | | | | |
| Untreated | 872.15 | 419.64 | 1077.56 | <LOQ | <LOQ | 28.16 | <LOQ | 150714.46 | 1496.32 |
| 1 | 771.8 | 488.1 | 799.2 | 532.6 | 12.02 | 15.2 | <LOQ | 26247.1 | 249.3 |
| 2 | 618.25 | 292.2 | 722.4 | 360.1 | <LOQ | 20.4 | <LOQ | 12919.2 | 145.7 |
| 3 | 698.0 | 422.9 | 796.9 | 433.9 | <LOQ | 24.9 | <LOQ | 26446.6 | 215.1 |
| 4 | 791.8 | 390.4 | 859.9 | 490.0 | 12.8 | 20.5 | <LOQ | 35633.5 | 324.4 |
| 5 | 709.3 | 371.1 | 735.4 | 453.2 | <LOQ | 25.8 | <LOQ | 17064.2 | 156.8 |
| 6 | 977.8 | 636.8 | 1000.3 | 634.7 | <LOQ | 38.8 | <LOQ | 21485.5 | 225.7 |
| 7 | 774.1 | 432.3 | 763.9 | 475.5 | 33.6 | 19.4 | <LOQ | 46755.4 | 380.0 |
| 8 | 893.7 | 505.5 | 1114.6 | 608.3 | <LOQ | 30.1 | <LOQ | 25647.4 | 208.2 |
| 9 | 725.1 | 462.0 | 583.3 | 515.1 | <LOQ | 25.5 | <LOQ | 12098.3 | 147.7 |
| 10 | 945.9 | 565.2 | 739.3 | 579.3 | <LOQ | 28.6 | <LOQ | 15353.4 | 175.9 |

TABLE H

Total heavy metals in the untreated and post-treated soil (soil 1 to 10).

| Soil | As | Ba | Cd | Co | Cr | Hg | Ni | Pb |
|---|---|---|---|---|---|---|---|---|
| | | | | mg·Kg$^{-1}$ | | | | |
| Untreated | 6.8 | 169.6 | 96.63 | <LOQ | 31.46 | <LOQ | 151.52 | 92.33 |
| 1 | <LOQ | 25.69 | <LOQ | <LOQ | <LOQ | <LOQ | <LOQ | <LOQ |
| 2 | <LOQ | 22.1 | <LOQ | <LOQ | <LOQ | <LOQ | <LOQ | <LOQ |
| 3 | <LOQ | 23.5 | <LOQ | <LOQ | <LOQ | <LOQ | <LOQ | <LOQ |
| 4 | <LOQ | 31.2 | <LOQ | <LOQ | <LOQ | <LOQ | <LOQ | <LOQ |
| 5 | <LOQ | <LOQ | <LOQ | <LOQ | <LOQ | <LOQ | <LOQ | <LOQ |

TABLE H-continued

Total heavy metals in the untreated and post-treated soil (soil 1 to 10).

| Soil | Analyte | | | | | | | |
|---|---|---|---|---|---|---|---|---|
| | As | Ba | Cd | Co | Cr | Hg | Ni | Pb |
| | | | | | $mg \cdot Kg^{-1}$ | | | |
| 6 | <LOQ | 35.0 | <LOQ | <LOQ | <LOQ | <LOQ | <LOQ | <LOQ |
| 7 | <LOQ | 37.4 | <LOQ | <LOQ | <LOQ | <LOQ | <LOQ | <LOQ |
| 8 | <LOQ | 30.3 | <LOQ | <LOQ | <LOQ | <LOQ | <LOQ | <LOQ |
| 9 | <LOQ | 26.4 | <LOQ | <LOQ | <LOQ | <LOQ | <LOQ | <LOQ |
| 10 | <LOQ | 32.0 | <LOQ | <LOQ | <LOQ | <LOQ | <LOQ | 11.5 |

In relation to heavy metals (Table H) it was observed that the biodigestion process was effective, varying according to the biodigester (1 to 10). The levels of heavy metals were lower in all the treated soils in relation the untreated soil, having lower levels than the limits of quantification (LOQ) in most of the soils. These results were satisfactory since the heavy metals can promote damage to human health and plant germination.

Two different plants were cultivated in post-treated soils namely crotalaria (*Crotalaria ledermannii*) and corn (*Zea mays*). The data of the total mineral nutrients of the plants are shown in Table I. In the same plant, variations in mineral levels were observed across soil samples. Comparisons between two plants showed a substantial variation only in the level of Ca.

TABLE I

Total mineral nutrients in plants cultivated in post-treated soils.

| Soil | Plant | Analyte | | | | | | | | |
|---|---|---|---|---|---|---|---|---|---|---|
| | | P | K | Ca | Mg | B | Zn | Cu | Fe | Mn |
| | | | | | | $mg \cdot Kg^{-1}$ | | | | |
| 1 | Crotalaria | 4359.79 | 10779.39 | 18369.42 | 2876.96 | <LOQ | 13.09 | <LOQ | 121.02 | 98.86 |
| | Corn | 4341.71 | 16217.39 | 4723.46 | 2774.7 | <LOQ | <LOQ | <LOQ | 265.88 | 72.19 |
| 2 | Crotalaria | 5204.97 | 10754.54 | 17854.37 | 2716.17 | <LOQ | 22.97 | <LOQ | 67.4 | 53.67 |
| | Corn | 5666.29 | 15114.01 | 6322.43 | 3563.13 | <LOQ | <LOQ | <LOQ | 155.47 | 49.03 |
| 3 | Crotalaria | 3648.49 | 12009.4 | 20977.2 | 2944.26 | <LOQ | 17.21 | <LOQ | 152.36 | 63.97 |
| | Corn | 3517.58 | 10915.01 | 5568.61 | 3165.7 | <LOQ | <LOQ | <LOQ | 206.48 | 49.52 |
| 4 | Crotalaria | 4086.17 | 10336.48 | 19300.41 | 2732.33 | <LOQ | 20.07 | <LOQ | 121.6 | 75.4 |
| | Corn | 3849.17 | 2893.71 | 7637.56 | 4147.09 | <LOQ | <LOQ | <LOQ | 95.24 | 74.61 |
| 5 | Crotalaria | 4914.45 | 12494.72 | 21730.14 | 2728.76 | <LOQ | 17.09 | <LOQ | 120.8 | 62.36 |
| | Corn | 4057.7 | 10124.37 | 8193.58 | 4689.77 | <LOQ | <LOQ | <LOQ | 253.33 | 103.6 |
| 6 | Crotalaria | 4350.62 | 11973.19 | 22402.96 | 2523.76 | <LOQ | 17.15 | <LOQ | 141.46 | 129.66 |
| | Corn | 5074.73 | 13492.98 | 5645.55 | 3503.69 | <LOQ | <LOQ | <LOQ | 164.1 | 49.61 |
| 7 | Crotalaria | 3195.64 | 11905.94 | 17220.27 | 3082.17 | <LOQ | 21.79 | <LOQ | 85.05 | 73.24 |
| | Corn | 4296.26 | 11783.0 | 7314.68 | 3372.72 | <LOQ | <LOQ | <LOQ | 300.59 | 99.16 |
| 8 | Crotalaria | 3327.67 | 10586.27 | 25545.1 | 2897.39 | <LOQ | 18.98 | <LOQ | 171.66 | 133.07 |
| | Corn | 4490.48 | 10770.18 | 6444.54 | 3299.36 | <LOQ | <LOQ | <LOQ | 98.42 | 84.7 |
| 9 | Crotalaria | 5446.21 | 11476.8 | 24115.48 | 2621.56 | <LOQ | 28.14 | <LOQ | 81.16 | 125.58 |
| | Corn | 4103.22 | 12791.6 | 5796.83 | 2628.99 | <LOQ | <LOQ | <LOQ | 120.75 | 55.0 |
| 10 | Crotalaria | 4501.07 | 10537.75 | 24560.32 | 3217.85 | <LOQ | 46.31 | <LOQ | 143.24 | 270.09 |
| | Corn | 3205.46 | 11668.52 | 5630.84 | 2313.39 | <LOQ | <LOQ | <LOQ | 154.71 | 90.52 |

Total heavy metal analysis (Table J) showed lower levels than the limits of quantification (LOQ) for most of the samples, in accordance with the data from the post-treatment of soils.

TABLE J

Total heavy metals in plants cultivated in post-treated soils.

| Soil | Plant | Analyte | | | | | | | |
|---|---|---|---|---|---|---|---|---|---|
| | | As | Ba | Cd | Co | Cr | Hg | Ni | Pb |
| | | | | | | $mg \cdot Kg^{-1}$ | | | |
| 1 | Crotalaria | <LOQ | <LOQ | <LOQ | <LOQ | <LOQ | <LOQ | <LOQ | <LOQ |
| | Corn | <LOQ | <LOQ | <LOQ | <LOQ | <LOQ | <LOQ | <LOQ | <LOQ |
| 2 | Crotalaria | <LOQ | <LOQ | <LOQ | <LOQ | <LOQ | <LOQ | <LOQ | <LOQ |
| | Corn | <LOQ | <LOQ | <LOQ | <LOQ | <LOQ | <LOQ | <LOQ | <LOQ |
| 3 | Crotalaria | <LOQ | 3.26 | <LOQ | <LOQ | <LOQ | <LOQ | <LOQ | <LOQ |
| | Corn | <LOQ | <LOQ | <LOQ | <LOQ | <LOQ | <LOQ | <LOQ | <LOQ |

TABLE J-continued

Total heavy metals in plants cultivated in post-treated soils.

| | | Analyte | | | | | | | |
|---|---|---|---|---|---|---|---|---|---|
| | | As | Ba | Cd | Co | Cr | Hg | Ni | Pb |
| Soil | Plant | | | | mg · Kg$^{-1}$ | | | | |
| 4 | Crotalaria | <LOQ | 20.58 | <LOQ | <LOQ | <LOQ | <LOQ | <LOQ | <LOQ |
|   | Corn | <LOQ | <LOQ | <LOQ | <LOQ | <LOQ | <LOQ | <LOQ | <LOQ |
| 5 | Crotalaria | <LOQ | 22.23 | <LOQ | <LOQ | <LOQ | <LOQ | <LOQ | <LOQ |
|   | Corn | <LOQ | <LOQ | <LOQ | <LOQ | <LOQ | <LOQ | <LOQ | <LOQ |
| 6 | Crotalaria | <LOQ | 48.22 | <LOQ | <LOQ | <LOQ | <LOQ | <LOQ | <LOQ |
|   | Corn | <LOQ | <LOQ | <LOQ | <LOQ | <LOQ | <LOQ | <LOQ | <LOQ |
| 7 | Crotalaria | <LOQ | 33.71 | <LOQ | <LOQ | <LOQ | <LOQ | <LOQ | <LOQ |
|   | Corn | <LOQ | <LOQ | <LOQ | <LOQ | <LOQ | <LOQ | <LOQ | <LOQ |
| 8 | Crotalaria | <LOQ | 17.26 | <LOQ | <LOQ | <LOQ | <LOQ | <LOQ | <LOQ |
|   | Corn | <LOQ | 7.46 | <LOQ | <LOQ | <LOQ | <LOQ | <LOQ | <LOQ |
| 9 | Crotalaria | <LOQ | 24.82 | <LOQ | <LOQ | <LOQ | <LOQ | <LOQ | <LOQ |
|   | Corn | <LOQ | <LOQ | <LOQ | <LOQ | <LOQ | <LOQ | <LOQ | <LOQ |
| 10 | Crotalaria | <LOQ | 58.51 | <LOQ | <LOQ | <LOQ | <LOQ | <LOQ | <LOQ |
|   | Corn | <LOQ | <LOQ | <LOQ | <LOQ | <LOQ | <LOQ | <LOQ | <LOQ |

In light of the foregoing and as mentioned above, the present disclosure's methods for bioremediation of heavy metal contaminated soil via anaerobic digestion provide an unexpected but needed advancement in the current bioremediation technologies.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Approximating language, as used herein throughout the specification and claims, may be applied to modify any quantitative representation that could permissibly vary without resulting in a change in the basic function to which it is related. Accordingly, a value modified by a term or terms, such as "about", "approximately" and "substantially", are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise. "Approximately" or "about" as applied to a particular value of a range applies to both values, and unless otherwise dependent on the precision of the instrument measuring the value, may indicate +/−10% of the stated value(s).

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiments were chosen and described in order to best explain the principles of the disclosure and the practical application, and to enable others of ordinary skill in the art to understand the disclosure for various embodiments with various modifications as are suited to the particular use contemplated.

I claim:

1. A method of treating a heavy metal contaminated soil comprising:
   contacting the contaminated soil with a bioremediation mixture for a predetermined time such that the contaminated soil is anaerobically digested,
   wherein the contaminated soil contains one or more heavy metals and is in contact with the bioremediation mixture,
   wherein the anaerobically digested soil has an available phosphorus level of greater than 45 milligrams per cubic decimeter ($mg/dm^3$), and a pH of 6-6.5, and contains a lesser amount of the one or more heavy metals than the contaminated soil, and
   wherein the bioremediation mixture includes at least one bacterium, at least one fungus, at least one nitrogen source, and at least one carbon source, wherein the at least one carbon source is different from the at least one nitrogen source.

2. The method of claim 1, wherein the one or more heavy metals are one or more selected from the group consisting of As, Ba, Cd, Co, Cr, Hg, Ni and Pb.

3. The method of claim 1, wherein one of the at least one carbon sources is *Lithothamnium calcareum*.

4. The method of claim 3, wherein, in addition to *Lithothamnium calcareum*, the at least one carbon source includes one or more selected from the group consisting of ash, bamboo, sawdust, trumpetwood, sugarcane bagasse and *Brachiaria* grass.

5. The method of claim 1, wherein the predetermined time is a number of days within a range of from 5 days to 35 days.

6. The method of claim 1, wherein the lesser amount of the one or more heavy metals is an amount sufficient to grow one or more plants suitable for human consumption.

7. The method of claim 1, wherein the anaerobically digested soil contains a given heavy metal in an amount lower than a limit of quantification for the given heavy metal.

8. The method of claim 1, wherein the contacting the contaminated soil with the bioremediation mixture comprises mixing the contaminated soil with the bioremediation mixture in a bioreactor such that the contaminated soil is anaerobically digested.

9. The method of claim 1, wherein the at least one nitrogen source is one or more selected from the group consisting of fish, sugar cane juice and cow dung.

10. The method of claim 1, wherein the at least one fungus includes one or more selected from the group consisting of fungal sp. 2686 YZ-2011, fungal sp. Griff. DX-FIR1, *Scedosporium dehoogii*, Podospora comunis, Preussia sp. BSH2.9, Meyerozima caribbica, *Epicoccum* sorghinum, *Fusarium* sp. FPGLX04, *Saccharomyces cerevisiae*, Geomyces sp. 12NJ08, *Zygosaccharomyces rouxii*, *Cladosporium halotolerans*, Phaeosphaeria sp.HKC12, *Mortierella exigua*, *Scedosporium apiospermum*, Podospora *decipiens*, Orpinomyces sp. NIANP57, Pleosporales sp. PANB1a0818P30CC484, and Uncultured Orpinomyces.

11. The method of claim 10, wherein the at least one bacterium includes one or more selected from the group consisting of uncultured bacterium, uncultured Bacteroidetes bacterium, *Petrimonas sulfuriphila*, uncultured soil bacterium, *Methanocorpusculum labreanum Z*, *Bacteroides paurosaccharolyticus*, and *Bacteroides graminisolvens*.

12. The method of claim 1, wherein the anaerobically digested soil has a cation exchange capacity (CEC) in a range of 8.27-11.21 centimol positive charge per cubic decimeter of soil ($cmolc/dm^3$).

13. A method of providing verified, decontaminated soil comprising:
   anaerobically digesting a heavy metal contaminated soil by contacting the contaminated soil with a bioremediation mixture for a first predetermined time, wherein the contaminated soil contains one or more heavy metals and is in contact with the bioremediation mixture,
   planting at least one test crop in at least a portion of the anaerobically digested soil and allowing for crop maturation for a second predetermined time, testing at least a portion of the mature crop for a level of heavy metal contamination, and verifying that the anaerobically digested soil is decontaminated if the level of heavy metal contamination is zero or below a predetermined threshold, wherein the bioremediation mixture includes at least one bacterium, at least one fungus, at least one nitrogen source, and at least one carbon source, wherein the at least one carbon source is different from the at least one nitrogen source, and wherein the anaerobically digested soil has an available phosphorus level of greater than 45 milligrams per cubic decimeter ($mg/dm^3$), and a pH of 6-6.5.

14. The method of claim 13, wherein the heavy metal contaminated soil contains one or more heavy metals selected from the group consisting of As, Ba, Cd, Co, Cr, Hg, Ni and Pb.

15. The method of claim 13, wherein one of the at least one carbon sources is *Lithothamnium calcareum*.

16. The method of claim 15, wherein, in addition to *Lithothamnium calcareum*, the at least one carbon source includes one or more selected from the group consisting of ash, bamboo, sawdust, trumpetwood, sugarcane bagasse and *Brachiaria* grass.

17. The method of claim 13, wherein the at least one nitrogen source is one or more selected from the group consisting of fish, sugar cane juice and cow dung.

18. The method of claim 13, wherein the first predetermined time is a number of days within a range of from 5 days to 35 days.

19. The method of claim 13, wherein the test crop is one or more of corn and *crotalaria*.

20. The method of claim 13, wherein the second predetermined time is a number of days within a range of 45 days to 75 days.

* * * * *

SEQUENCE LISTING

<160> NUMBER OF SEQ ID NOS: 4

<210> SEQ ID NO 1
<211> LENGTH: 17
<212> TYPE: DNA
<213> ORGANISM: Artificial sequence
<220> FEATURE:
<223> OTHER INFORMATION: Primer 341F for amplifying V3-V4 region of rRNA
      16S

<400> SEQUENCE: 1
cctacgggrs gcagcag                                                  17

<210> SEQ ID NO 2
<211> LENGTH: 20
<212> TYPE: DNA
<213> ORGANISM: Artificial sequence
<220> FEATURE:

```
<223> OTHER INFORMATION: Primer 806R for amplifying V3-V4 region of rRNA
      16S

<400> SEQUENCE: 2
ggactachvg ggtwtctaat                                                      20

<210> SEQ ID NO 3
<211> LENGTH: 18
<212> TYPE: DNA
<213> ORGANISM: Artificial sequence
<220> FEATURE:
<223> OTHER INFORMATION: Primer ITS1 for amplifying ITS1 region

<400> SEQUENCE: 3
gaaccwgcgg arggatca                                                        18

<210> SEQ ID NO 4
<211> LENGTH: 20
<212> TYPE: DNA
<213> ORGANISM: Artificial sequence
<220> FEATURE:
<223> OTHER INFORMATION: Primer ITS2 for amplifying ITS1 region

<400> SEQUENCE: 4
gctgcgttct tcatcgatgc                                                      20
```